US011638831B2

(12) United States Patent
Zamar

(10) Patent No.: US 11,638,831 B2
(45) Date of Patent: May 2, 2023

(54) TREATMENT OF PSYCHIATRIC CONDITIONS SUCH AS RESISTANT DEPRESSION, BIPOLAR DISORDER AND/OR MAJOR DEPRESSIVE DISORDER VIA APPLICATION OF REPETITIVE TRANSCRANIAL MAGNETIC STIMULATION WITH THYROID HORMONE TREATMENT AND/OR QUETIAPINE

(71) Applicant: THE LONDON PSYCHIATRY CENTRE, London (GB)

(72) Inventor: Antonios Zamar, London (GB)

(73) Assignee: THE LONDON PSYCHIATRY CENTRE, Greater London (GB)

( * ) Notice: Subject to any disclaimer, the term of this patent is extended or adjusted under 35 U.S.C. 154(b) by 286 days.

(21) Appl. No.: 16/769,895

(22) PCT Filed: Dec. 14, 2018

(86) PCT No.: PCT/GB2018/053634
§ 371 (c)(1),
(2) Date: Jun. 4, 2020

(87) PCT Pub. No.: WO2019/116048
PCT Pub. Date: Jun. 20, 2019

(65) Prior Publication Data
US 2020/0384279 A1    Dec. 10, 2020

(30) Foreign Application Priority Data

Dec. 14, 2017  (GB) ...................................... 1720816
Dec. 1, 2018   (GB) ...................................... 1819647

(51) Int. Cl.
*A61P 25/24*    (2006.01)
*A61N 2/00*     (2006.01)
(Continued)

(52) U.S. Cl.
CPC ............ *A61N 2/002* (2013.01); *A61B 5/0245* (2013.01); *A61B 5/4848* (2013.01);
(Continued)

(58) Field of Classification Search
CPC .......... A61N 2/002; A61N 2/006; A61N 2/02; A61B 5/0245; A61B 5/4848;
(Continued)

(56) References Cited

U.S. PATENT DOCUMENTS

2003/0104041 A1*  6/2003  Hsu ...................... A61K 8/0208
                                                          424/722
2003/0228628 A1* 12/2003  Powell ............... G01N 33/6896
                                                          435/7.1
(Continued)

OTHER PUBLICATIONS

Abraham, G., "Combined Transcranial Magnetic Stimulation and Right Unilateral Electroconvulsive Therapy in Patients With Treatment-Refractory Depression", Can J Psychiatry, vol. 49, No. 6, p. 412 (2004).

(Continued)

*Primary Examiner* — Amanda K Hulbert
*Assistant Examiner* — Natasha Patel
(74) *Attorney, Agent, or Firm* — Heslin Rothenberg Farley & Mesiti P.C.

(57) ABSTRACT

The present invention relates to treatment of a psychiatric condition, for example resistant depression (RD), bipolar disorder (either threshold or sub-threshold) and/or major depressive disorder via application of repetitive transcranial magnetic stimulation with a drug treatment, in particular application of repetitive transcranial magnetic stimulation with treatment to modulate the activity of the neurones and induce neuroplasticity and the use of Thyroid hormone treatment to increase quantity or activity of thyroid hormones, for example for treatment of thyroid dysfunction.

(Continued)

Figure 1:
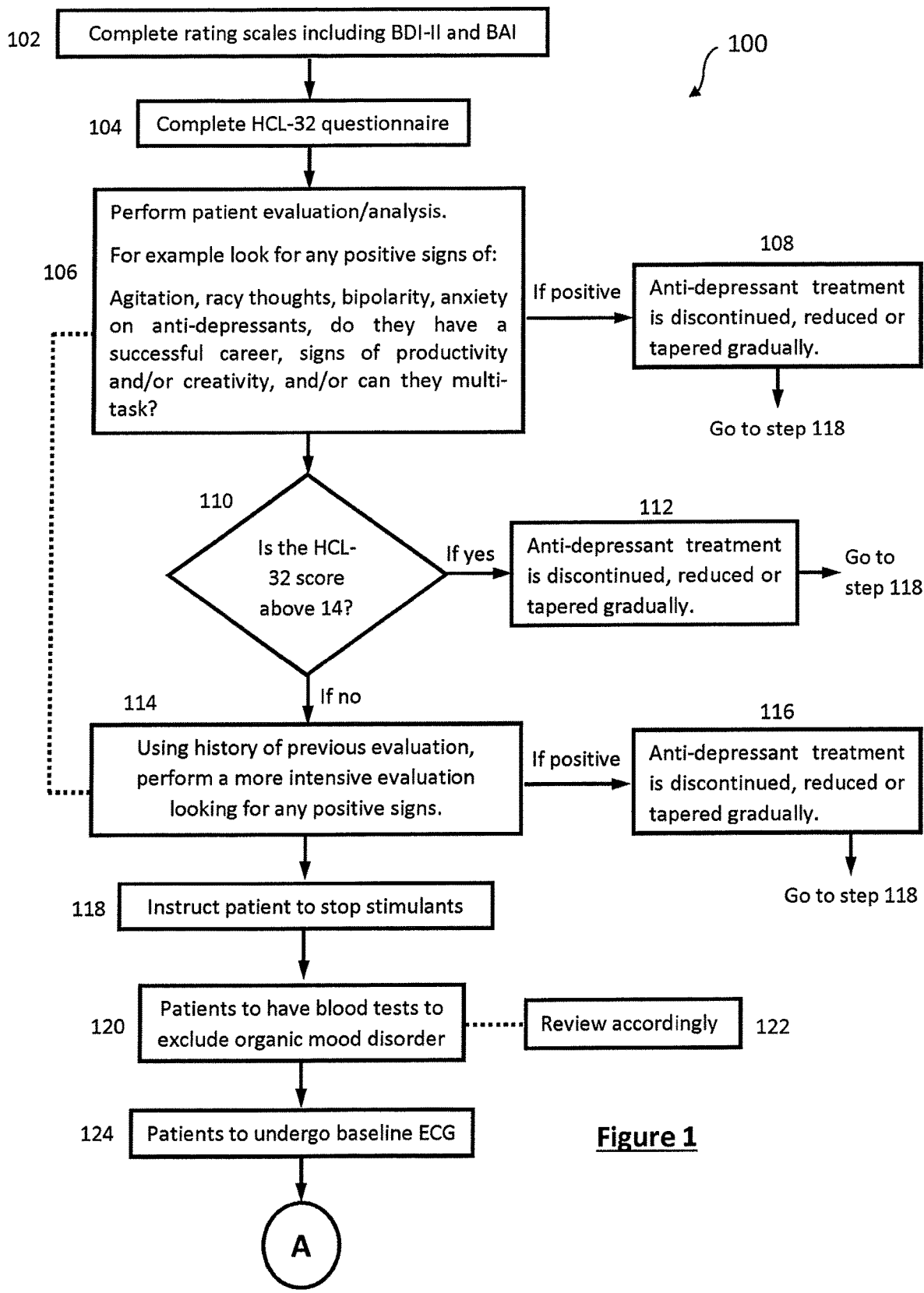

Patients may be selected for treatment by testing for the presence of normal thyroid function.

20 Claims, 2 Drawing Sheets

(51) Int. Cl.
| | |
|---|---|
| *A61B 5/0245* | (2006.01) |
| *A61B 5/00* | (2006.01) |
| *A61K 31/198* | (2006.01) |
| *A61K 31/554* | (2006.01) |
| *A61N 2/02* | (2006.01) |
| *C12Q 1/6883* | (2018.01) |
| *G01N 33/78* | (2006.01) |

(52) U.S. Cl.
CPC .......... *A61K 31/198* (2013.01); *A61K 31/554* (2013.01); *A61N 2/006* (2013.01); *A61N 2/02* (2013.01); *A61P 25/24* (2018.01); *C12Q 1/6883* (2013.01); *A61B 5/4227* (2013.01); *C12Q 2561/00* (2013.01); *C12Q 2600/156* (2013.01); *G01N 33/78* (2013.01)

(58) Field of Classification Search
CPC .. A61B 5/4227; A61K 31/198; A61K 31/554; A61K 45/06; A61P 25/24; A61P 25/18; C12Q 1/6883; C12Q 2561/00; C12Q 2600/156; G01N 33/78
See application file for complete search history.

(56) References Cited

U.S. PATENT DOCUMENTS

| | | | | |
|---|---|---|---|---|
| 2007/0027483 A1* | 2/2007 | Maschino | .......... | A61N 1/36053 607/2 |
| 2007/0142874 A1* | 6/2007 | John | .......... | A61N 2/006 607/45 |
| 2010/0048455 A1* | 2/2010 | Clark | .......... | A61P 17/14 514/1.1 |
| 2011/0245092 A1* | 10/2011 | Bilello | .......... | C12Q 1/6883 702/19 |
| 2013/0267601 A1* | 10/2013 | Abramowitz | .......... | A61P 25/28 514/567 |

OTHER PUBLICATIONS

Bauer, M., "Thyroid hormone augmentation with levothyroxine in bipolar depression", Bipolar Disord, vol. 4, Suppl. 1, pp. 109-110 (2002).

Bing, H., et al., "Association of genetic polymorphisms in the type II deiodinase gene with bipolar disorder in a subset of Chinese population", Progress in Neuro-Psychopharmacology & Biological Psychiatry, vol. 33, pp. 986-990 (2009).

Krishna, V.N., et al., "Association between bipolar affective disorder and thyroid dysfunction", Asian Journal of Psychiatry, vol. 6, pp. 42-45 (2013).

Hu, S., et al., "Efficacy of repetitive transcranial magnetic stimulation with quetiapine in treating bipolar II depression: a randomized, double-blinded, control study", Scientific Reports, 6:30537, DOI: 10.1038/srep30537, pp. 1-7 (2016).

Szuba, M.P., et al., "Acute Mood and Thyroid Stimulating Hormone Effects of Transcranial Magnetic Stimulation in Major Depression", Society of Biological Psychiatry, vol. 50, pp. 22-27 (2001).

Zamar, A., et al., "High-dose levothyroxine for the management of bipolar affective disorder: two case reports", Journal of the Royal Society of Medicine Open, vol. 8, No. 9, pp. 1-2 (2017).

Zamar, A., et al., "High dose Levothyroxie (HDL) combined with repetitive Transcranial Magnetic Stimulation (rTMS) for Bipolar Disorder (BPD) with DIO2 gene polymorphisms", The London Psychiatry Centre, Health 121.

International Search Report and Written Opinion of the International Searching Authority for International Patent Application No. PCT/GB2018/053634 dated Dec. 14, 2018.

* cited by examiner

TREATMENT OF PSYCHIATRIC CONDITIONS SUCH AS RESISTANT DEPRESSION, BIPOLAR DISORDER AND/OR MAJOR DEPRESSIVE DISORDER VIA APPLICATION OF REPETITIVE TRANSCRANIAL MAGNETIC STIMULATION WITH THYROID HORMONE TREATMENT AND/OR QUETIAPINE

CROSS REFERENCE TO RELATED APPLICATIONS

This application is a National Stage filing under section 371 of International Application No. PCT/GB2018/053634, filed on Dec. 14, 2018 and published in English on Jun. 20, 2019 as WO2019/116048, and claims priority to Great Britain Patent Application No. 1720816.6, filed on Dec. 14, 2017, and Great Britain Patent Application No. 1819647.7, filed on Dec. 1, 2018. The entire disclosures of each of the prior applications are hereby incorporated by reference herein.

FIELD OF THE INVENTION

The present invention relates to treatment of a psychiatric condition, for example resistant depression (RD), bipolar disorder (either threshold or sub-threshold) and/or major depressive disorder via application of repetitive transcranial magnetic stimulation with a drug treatment, in particular application of repetitive transcranial magnetic stimulation with treatment to modulate the activity of the neurones and induce neuroplasticity and the use of Thyroid hormone treatment to increase quantity or activity of thyroid hormones, for example for treatment of thyroid dysfunction. Patients may be selected for treatment by testing for the presence of normal thyroid function.

BACKGROUND

Subthreshold and type 2 bipolar disorders carry a high depression burden, a significant suicide rate, and divorce rates of up to 90%. A large study conducted by the World Health Organisation in May 2008 found that in 15 countries bipolar disorder was 2-3 times more disabling than cancer, heart disease and arthritis.

Resistant depression (RD) is a common disorder with millions of sufferers around the world. Sufferers typically experience a wide range of symptoms including, a loss of interest or pleasure, feelings of sadness, guilt, low self-esteem, disturbances in sleep and appetite, poor concentration, and suicidal speculation.

Treatment with antidepressant medication is the most common and first line treatment for many patients suffering from RD, however a significant number of patients do not respond to antidepressant medication and indeed some deteriorate with antidepressants.

The inventor has developed a new combination treatment which effectively treats these debilitating disorders.

SUMMARY OF THE INVENTION

The present invention is directed to a rTMS protocol or treatment regimen for bipolar disorder and resistant depression (RD) to further improve the outcomes in real life patients, and provide patients with the best possible treatment.

Suitably the present invention may provide an improved method of modulating a brain activity of a patient. Advantageously the present invention may provide an improved clinical procedure for use in the treatment of a psychiatric condition, for example bipolarity or resistant depression. Further the present invention can provide an apparatus for modulating a brain activity of a human patient. Suitably the present invention provides an apparatus for performing a clinical procedure for use in the treatment of bipolarity or resistant depression.

Without wishing to be bound by theory, suitably a psychiatric condition to be treated may be caused or correlated with a deficiency in thyroid hormone, thyroid activation or one or more enzymes involved in thyroid hormone production or activation or proteins responsible for intracellular transport of thyroid hormones. The London Psychiatry Centre team found through genetic testing that more than 90% of the bipolar cases randomly and consecutively tested have a deficiency of one or both enzymes needed to activate thyroid hormone in the brain and the body, as well as a deficiency in a thyroid hormone transmembrane transporter protein. Patients who had the combination of rTMS (Repetitive Transcranial Magnetic Stimulation) and high dose thyroid drug treatment saw their condition recover fully after years of unsuccessful treatment with drugs, with the age ranges of patients being between 15 and 80-years-old. This effective new process also displays generally a lack of or minimal side effects. It is hypothesised by the inventors that the thyroid medication addresses the cerebral thyroid deficiency and the rTMS forms new neural pathways allowing for more stable remission in the long term through neuroplasticity.

According to the present invention, there is provided a method of modulating a brain activity of a human patient, the method comprising: performing patient evaluation to determine symptoms of a psychiatric condition; and subjecting a patient to a repetitive transcranial magnetic stimulation (rTMS), the rTMS occurring at a concentrated region of the scalp, at preferred electromagnetic frequency, and for a time sufficient to modulate said brain activity wherein an improvement in a psychiatric condition is achieved. This provides an improved brain modulation technique whereby patients with a psychiatric condition such as bipolar disorder (either threshold or sub-threshold) and/or major depressive disorder, who could theoretically deteriorate on antidepressants (productive, creative, successful individuals), are treated in a specific way to ensure better results.

A method of the invention may comprise modulating a brain activity of a human patient, wherein the patient has been evaluated as having symptoms of a psychiatric condition; wherein the step of modulating brain activity is provided by subjecting the patient to a repetitive transcranial magnetic stimulation (rTMS), optionally the rTMS occurring at a concentrated region of the scalp, optionally at preferred electromagnetic frequency, and for a time sufficient to modulate said brain activity. Suitably modulation of brain activity provides for an improvement in a psychiatric condition of a patient. The rTMS is performed in combination with treatment with a medicament for treating depression for example quetiapine and/or thyroid hormone deficiency/dysfunction, for example, thyroxine, liothyronine, levothyroxine, or levothyroxine sodium.

According to a further aspect of the invention there is provided a method of modulating a brain activity of a human patient, wherein the method comprises the step of evaluating a patient as having a deficiency or dysfunction in thyroid hormone, thyroid activation or one or more enzymes involved in thyroid hormone production or activation or a dysfunction of carrier protein(s) of thyroid hormones and/or their derivatives. This step allows the targeting of patients who will benefit from treatment. The step of modulating brain activity is provided by subjecting the patient to a repetitive transcranial magnetic stimulation (rTMS), optionally the rTMS occurring at a concentrated region of the scalp, optionally at preferred electromagnetic frequency, and for a time sufficient to modulate said brain activity.

The rTMS may be performed in combination with treatment with a medicament for treating depression for example quetiapine and/or thyroid hormone deficiency/dysfunction, for example, thyroxine, levothyroxine, Liothyronine or levothyroxine sodium. The quetiapine may not always be needed depending on the patient presentation and acceptance.

According to a further aspect of the invention there is provided a method of modulating a brain activity of a human patient, wherein the patient has been evaluated as having a deficiency in thyroid hormone, thyroid activation or one or more enzymes involved in thyroid hormone production or activation or any of its carriers; wherein the step of modulating brain activity is provided by subjecting the patient to a repetitive transcranial magnetic stimulation (rTMS), optionally the rTMS occurring at a concentrated region of the scalp, optionally at preferred electromagnetic frequency, and for a time sufficient to modulate said brain activity.

The rTMS may be performed in combination with treatment with a medicament for treating depression for example quetiapine and/or Thyroid hormone dysfunction, for example thyroxine, liothyronine, levothyroxine, or levothyroxine sodium. Quetiapine may not be needed depending on the patient presentation.

The above medicaments may be combined. For example, thyroxine and/or liothyronine with rTMS; or thyroxine and quetiapine with rTMS; or liothyronine and quetiapine with rTMS; or thyroxine and/or liothyronine and quetiapine with rTMS The described treatments herein may be used with patients who are bipolar or present with resistant depression or ADHD.

DETAILED DESCRIPTION

Terms of Art

TSH=THYROID STIMULATING HORMONE

This hormone comes from the pituitary to stimulate the thyroid gland into making more hormone. TSH rises when the thyroid is struggling.

The approx. reference range for this test is 0.27-4.2 mIU/L.

TT4=TOTAL T4

Thyroid hormones bound to proteins. TT4 lowers when the thyroid is struggling.

The approx. reference range for this test is 50 to 160.

FT4=FREE T4

Thyroid hormones not bound to proteins. FT4 lowers when the thyroid is struggling.

The approx. reference range for this test is 12.0 to 22.0 pmol/L

FT3=FREE T3

T4 converts to T3 and is the only thyroid hormone actually used by the body's cells.

The approx. reference range for Free T3 is 3.1 to 6.8 pmol/L.

rT3=REVERSE T3

This is produced as a result of removal of a different iodine ring by Deiodinase 3 and has a reference range of 9-25 ng/dl. RT3 competes with T3 at the cellular level.

DIO1 Iodothyronine Deiodinase 1

The DIO1 gene encodes the enzyme type 1 iodothyronine deiodinase, a selenoprotein requiring selenium for its synthesis. DIO1 catalyzes the activation, as well as the inactivation of thyroid hormone. The activation reaction catalyzes the conversion of the prohormone thyroxine (T4), secreted by the thyroid gland, to the bioactive thyroid hormone (T3). This gene is predominantly expressed in the liver and kidney and provides most of the circulating T3m which is essential for growth, differentiation and basal metabolism.

DIO2 Iodothyronine Deiodinase 2

The DIO2 gene encodes the enzyme type II iodothyronine deiodinase, a selenoprotein requiring selenium for its synthesis. DIO2 catalyzes the conversion of T4 to T3 like DIO1. However, this gene is expressed in the thyroid, placenta, pituitary and brain.

Carrier Proteins

The carrier proteins may be any of the thyroid hormone transmembrane transporters. Facilitated uptake and release of TH by TH transmembrane transporters (THTT) is essential for their intracellular availability.

As will be appreciated in the art, thyroid hormones are typically considered to be hormones produced and released by the thyroid gland, namely thyroxine (T4) which is activated to triiodothyronine(T3) through Deiodinases 1 and 2 and reverse T3 (rT3) through deiodinase enzyme 3 including DIO1 variant rs2235544 34C>A and DiO2 variant rs12885300 Gly3Asp but not excluding others. For example, such as Dio3 or other variants; or transporters including rs225014 Thr92ala or other transporters.

Diagnosis of Thyroid Hormone Deficiency/Dysfunction

Prior to treatment with thyroid hormone, an analogue or another medicament for treating thyroid dysfunction, the patient may be tested for suitability for the treatment. For example, the patient can be tested for full thyroid function.

The test for checking thyroid functions can include a blood test, for example to test for the levels of any one or more of the following: TSH, Free T4 and Free T3. This test involves analysing the free-T4 and free-T3 ratio after administration of thyroxine, levothyroxine or an analogue or salt, whereby the free-T4 rise is substantially higher than the lagging free-T3 rise. rT3 also rises significantly in this population Additionally, or alternatively, an ECG can be performed to monitor tolerance to thyroid treatment as well as bone density scans and metabolomics In patients without thyroid enzyme dysfunction, the administration of thyroid hormone (thyroxine) causes T3 and T4 to rise exponentially together. The inventor has determined that in bipolar patients or those with resistant depression or ADHD, T4 rises dramatically but is not converted to T3. These patients are unable to activate normal doses of thyroid hormone.

For example, the free T4 may be 1.5, 2. 3, 4 or more times its normal concentration whilst free T3 rises modestly after the administration of thyroxine or levothyroxine.

If T3 rises exponentially to T4, reverse T3 also rises counteracting excess T3 levels, hence protecting from side effects of T3

The thyroxine or levothyroxine administered for the patient evaluation may comprise at least 50 mcg. Liothyronine doses are at least 10 mcgs.

Genetic Test

Suitably a method of identifying or evaluating one or more patients suitable for treatment may comprise the step of performing a genetic test to identify the presence or deficiency of one or more enzymes involved in thyroid hormone activation or production.

Conveniently, the genetic test may be performed to identify the presence or deficiency of at least one enzyme, suitably at least one of two enzymes, involved in thyroid hormone activation. Suitably the tests may detect a polymorphism(s) of DIO1 and/or DIO2. The test may also detect a polymorphism(s) in the DIO3 gene. Suitably a polymorphism may cause the presence or deficiency in quantity or activity in one or more enzymes involved in thyroid hormone activation in the brain or periphery.

Preferably, the genetic test is performed to identify the presence or deficiency of one or more enzymes involved in thyroid hormone activation in the brain, or the periphery optionally of proteins encoded by DIO1 and/or DIO2.

Conveniently, the genetic test identifies patients having difficulty in converting T4 (thyroxine) to T3 (active thyroid hormone). In embodiments, some patients have polymorphism present in the above DIO genes. In other embodiments mutations can be present in other genes in the pathway which also effect the T4/T3 ratio. For example, mutations in the intracellular carrier proteins of T3/T4.

Preferably, the genetic test is directed to identifying a Deiodinase enzyme deficiency. However, the inventor has found that patients without mutations in DIO1/2 enzymes also respond to treatment. It is hypothesised these patients may have further mutations in the carrier proteins for T3/T4 which also effect T3 levels.

A suitable genetic test for identifying SNPs in DIO1/2 is by Lifecode Gx (TM): https://www.lifecodegx.com/products/nervous-system. The SNPs tested in this kit include the following:

|  |  | Result | Description |
|---|---|---|---|
| DIO1 variant |  |  |  |
| rs2235544 | 34C > A | AA | Reduced conversion of T4 to T3. The A allele of this SNP is associated with lower deiodinase 1 function, lower free T3 and free T3/T4 ratio and higher serum free T4 and rT3. |
| DIO2 variant |  |  |  |
| rs12885300 | Gly3Asp | TC | T allele |
| Rs225014 | Thr92Ala | TT |  |

The inventor has found that over 90% of bipolar patients tested positive for 1 or more mutations in the DIO1/2 genes. The DIO1 gene is important as 20% of cerebral T3 comes from peripheral DiO1 activity and 80% is derived from central (brain) DiO2 activity.

Other suitable tests include testing for SNPs for carrier proteins of T4 and/or T3 as explained above. The inventor has found that patients without mutations in DIO1/2 still respond to treatment. The inventor hypothesises that this is as a result of mutation in the various carrier proteins that transport T3 into the cell.

rTMS Protocol

Conveniently, the method may provide for rTMS that at different concentrated regions of the scalp.

In embodiments, different concentrated regions of the scalp comprise a substantially left dorsolateral prefrontal cortex (DLPFC) region or a substantially right dorsolateral prefrontal cortex (DLPFC) region.

Conveniently, the preferred electromagnetic frequency used in the methods herein is below about 20.1 Hz. Suitably, the preferred electromagnetic frequency is above about 0.9 Hz. For example, any range between 0.9, 1, 2, 3, 4, 5, 6, 7, 8, 9, 10, 11, 12, 13, 14, 15, 16, 17, 18, 19 and 20.1 Hz.

The rTMS protocol may vary depending on the psychiatric condition. For example, the left side of the brain may be targeted (for example, left DLFPC region of the scalp) when the patient is flatly depressed. The frequency is optimally 10 Hz. iTBS may be used in place of traditional rTMS.

The right side of the brain (for example the right region DLPFC of the scalp) may be targeted when the patient is diagnosed as having a mixed condition (mixed bipolar, agitated depression, depression with flight of ideas or any variant of mixed depression and RD); or when the patient is subthreshold bipolar or rapid cycling bipolar. Optimally the frequency is 1 Hz. cTBS may be used instead of traditional rTMS.

As described above suitably rTMS may be provided as iTBS (Intermittent (theta burst rTMS)). Suitably rTMS may be provided as cTBS (continuous theta burst rTMS). iTBS may be administered if the patient is depressed. Intermittent (theta burst rTMS) that mimics the brain's natural rhythms and takes just over three minutes per treatment compared with 25 minutes for standard rTMS which exerts a stimulating effect; or cTBS may be administered if mixed presentation, bipolar or diagnosed with ADHD (cTBS is continuous theta burst stimulation which exerts an inhibitory effect).

rTMS may be performed daily for 1, 2, 3, 4 or 5 days/week for 3, 4, 5 or 6 weeks. After this initial protocol, further maintenance sessions can be carried out. The rTMS session may last 10, 15, 20, 25, 30 or 35 minutes. For example, rTMS may be performed for 25 minutes daily for 5 days/week for 4-6 weeks.

According to a further aspect of the present invention there is provided a method of modulating a brain activity of a human patient, the method comprising: performing patient evaluation to determine symptoms of a psychiatric condition; and administering repetitive transcranial magnetic stimulation in alternate frequencies; the one of the alternate comprising a first electromagnetic frequency and the other one of the alternate comprising a second electromagnetic frequency; wherein the one of the alternate comprises a first electromagnetic frequency less than the other one of the alternate comprising a second electromagnetic frequency. This provides an improved brain modulation technique whereby patients with a psychiatric condition such as bipolar disorder (either threshold or subthreshold) and/or major depressive disorder, who could theoretically deteriorate on antidepressants (productive, creative, successful individuals), are treated in a specific way to ensure better results. By alternate is meant different electromagnetic frequencies in different sessions. For example, depending on the clinical outlook, depression is treated with the 10 Hz rTMS (or iTBS) left-side simulation and anxiety and/or mixed states is treated with the 1 Hz rTMS (or cTBS) right-side stimulation. A feature is to reduce the anxiety and/or mixed stated with the 1 Hz treatment prior to the 10 Hz treatment. However 1 Hz treatment can be used after the 10 Hz treatment if mixed states and/or anxiety occur. That is, the treatment occurs in tandem.

Preferably, the one of the alternate electromagnetic frequency is substantially 1 Hz and the other one of the alternate electromagnetic frequency is substantially 10 Hz.

Conveniently, one of the alternate is performed at a substantially right region DLPFC of the scalp at an electromagnetic frequency of substantially 1 Hz and the other one of the alternate is performed at a substantially left DLFPC region of the scalp at an electromagnetic frequency of substantially 10 Hz.

Which of the frequencies is attempted first depends on the presentation of the patient. For example, if the patient is depressed then mixed presentation, a 10 Hz frequency is preferred first followed by a 1 Hz frequency. If the patient presents as bipolar initially and then depressed, then a 1 Hz frequency is tried first followed by a 10 Hz frequency. Generally the condition remits with one protocol, but both may have to be used in tandem if the presentation changes.

Suitably, the rTMS is performed in combination with a medicament as described above. It is considered this helps to provide an improved treatment experience.

Medicament for Use/Method for Treating

According to a further aspect of the present invention, there is provided a method of modulating a brain activity of a human patient, the method comprising: performing patient evaluation to determine symptoms of a psychiatric condition; and subjecting a patient to a repetitive transcranial magnetic stimulation (rTMS) in combination with a medicament, the rTMS in combination with the medicament occurring for a time sufficient to modulate said brain activity wherein an improvement in a psychiatric condition is achieved. This provides an improved brain modulation technique whereby patients with a psychiatric condition such as bipolar disorder (either threshold or sub-threshold) and/or major depressive disorder, who could theoretically deteriorate on antidepressants (productive, creative, successful individuals), are treated in a specific way to ensure better results.

The method may be suitable for treating bipolarity, resistant depression or ADHD.

Suitably, there is provided a method of modulating a brain activity of a human patient, wherein the patient has been evaluated as having symptoms of a psychiatric condition, the method comprising: subjecting the patient to a repetitive transcranial magnetic stimulation (rTMS) in combination with a medicament, the rTMS in combination with the medicament occurring for a time sufficient to modulate said brain activity wherein an improvement in a psychiatric condition is achieved.

In some cases the administration of medicament can be performed before rTMS treatment, in other cases it can be performed when a rTMS is started or terminated after rTMS treatment. In further cases it can be performed both before and after rTMS treatment. Medicaments can continue for life after rTMS is discontinued.

Suitable Medicaments

Suitably the medicament provides for a modulation in the amount of a thyroid hormone(s) to be provided to the subject/patient. Suitably modulation may be to provide the subject with levels of thyroid hormone(s) typically observed in a population not suffering from a psychiatric condition, or normal, increased or decreased levels of thyroid hormone(s) as required to provide for an improved psychiatric condition in the method. Suitably the medicament may be provided to alter the ratio of thyroid hormones to each other in the subject.

Preferably, the medicament is selected from a group consisting of a neuroleptic and a mood stabiliser. This provides for optimum treatment and for anti-depressant free treatment. Conveniently, in embodiments, the medicament comprises a combination of neuroleptics and mood stabilisers, excluding anti-depressants.

Preferably, the medicament is selected from at least one medicament selected from quetiapine, thyroxine, levothyroxine, (preferably as levothyroxine sodium). These have been found to be optimum medicaments and provide for an enhanced treatment experience. In some cases the administration of levothyroxine, liothyronine or otherwise thyroxine, or quetiapine can be started before rTMS treatment, in other cases it can be started during or after rTMS treatment. In all cases Levothyroxine may be continued after rTMS and quetiapine in some cases. The thyroxine and other thyroid hormone drug analogues increase the T3 availability in the brain thus treating the cerebral thyroid deficiency.

Optionally, the medicament comprises at least 25 mg of quetiapine.

Optionally, the medicament comprises at least 50 mcg of thyroxine.

Optionally, the medicament comprises at least 50 mcg of levothyroxine.

Optionally the medicament comprises at least 10 mcg of liothyronine

Optionally, the medicament comprises at least 50 mcg thyroxine, 10 mcg of Liothyronine and at least 25 mg of quetiapine.

Dosage is once daily but with quetiapine can be twice and liothyronine twice to 3 times daily.

Dosage may be increased to 100, 200, 300, 400, 500, 600, 700, 800, 900 or 1000 or more mcg daily.

With liothyroinine can be increased up to 160 mcgs daily and Quetiapine up to 800 mgs daily or according to blood levels.

An example protocol may be to begin the patient with thyroxine or another medicament for treating the cerebral thyroid deficiency, along with rTMS. The rTMS may vary depending on the presentation of the patient as explained below. Quetiapine can also be combined with the drug for treating the thyroid deficiency.

Questionnaire

According to a further aspect of the present invention, there is provided a method of performing a clinical procedure for use in the treatment of resistant depression, the method comprising: performing a first patient evaluation to determine symptoms of resistant depression, the first patient evaluation comprising: a patient interview; a Hypomania Symptom checklist (HCL-32) questionnaire completed by the patient; an observer interview; and family history; the method further comprising: administering rTMS to at least one concentrated scalp region of the patient, based on the result(s) of said evaluation. This provides an improved treatment protocol whereby patients with a psychiatric condition such as bipolar disorder (either threshold or sub-threshold) and/or major depressive disorder, who could theoretically deteriorate on antidepressants (productive, creative, successful individuals), are treated in a specific way to ensure better results. Following this protocol compared with other techniques has shown substantially high success in treatment resistant cases.

According to a further aspect of the present invention, there is provided a method of performing a clinical procedure for use in the treatment of resistant depression, the method comprising: administering rTMS to at least one concentrated scalp region of a patient evaluated to have symptoms of resistant depression, wherein a patient evaluation can have comprised one or more of: a patient interview; a Hypomania Symptom checklist (HCL-32) questionnaire completed by the patient; an observer interview; and family history. Suitably the patient may have been evaluated as having a psychiatric condition such as bipolar disorder (either threshold or sub-threshold) and/or major depressive disorder, for example a patient with a major depressive disorder who could theoretically deteriorate on antidepressants.

This provides an improved treatment protocol whereby patients with a psychiatric condition such as bipolar disorder (either threshold or sub-threshold) and/or major depressive disorder, who could theoretically deteriorate on antidepressants (productive, creative, successful individuals), are treated in a specific way to ensure better results. Following this protocol compared with other techniques has shown substantially high success in treatment resistant cases.

Preferably, a first patient evaluation may further comprise investigating for any one or more of:
(a) signs of sub-threshold racing thoughts;
(b) signs of bi-polarity;
(c) signs of mixed states;
(d) signs of insomnia;
(e) anxiety on previous or current anti-depressants;
(f) sub-threshold signs of racing thoughts;
(g) creativity;
(h) successful careers;
(i) academic performance;
(l) being able to perform tasks effectively before or together with depression;
(k) agitation;
(I) racy thoughts;
(m) signs of productivity; and
(n) if the patient can multi-task.

Preferably, the first patient evaluation is further used to determine if a patient has any one or more of: sub-threshold racing thoughts, creativity, successful careers, academic performance, being able to perform tasks effectively with depression, agitation, anxiety, and bipolarity.

Conveniently, upon determining the patient has any one or more of: sub-threshold racing thoughts, creativity, successful careers, academic performance, being able to perform tasks effectively with depression, agitation, anxiety, and bipolarity, the method further comprises any one or more of: discontinuation, reduction, gradual tapering, of patient anti-depressant drug treatment.

Preferably, upon determining the patient does not have any one or more of: sub-threshold racing thoughts, creativity, successful careers, academic performance, being able to perform tasks effectively with depression, agitation, anxiety, and bipolarity, the method further comprises analysing the patient HCL-32.

Conveniently, upon analysing the patient HCL-32, and upon the result of the patient HCL-32 being greater than 14, the method further comprises any one or more of: discontinuation, reduction, and gradual tapering of patient anti-depressant drug treatment.

Preferably, upon referring to the patient HCL-32, and upon the result of the patient HCL-32 being lower than 14 the method further comprises: performing a second evaluation; the second evaluation being used to determine if the patient has any one or more of: subthreshold racing thoughts, creativity, successful careers, academic performance, being able to perform tasks effectively with depression, agitation, anxiety, and bipolarity.

Conveniently, the second evaluation comprises investigating for any one or more of:
(a) a patient prospective mood chart;
(b) generally being jovial without exhibiting signs of bipolarity;
(c) a history of becoming any one or more of anxious, agitated with exposure to antidepressants;
(d) a history of any signs of slight mood elevation whether any one or more of sustained, episodic;
(e) the level of the patient premorbid functioning being higher than normal;
(f) a bipolar spectrum;
(g) premorbid ICD-10 subthreshold hypomania;
(h) mild signs of cyclothymia;
(i) sub-threshold bipolarity;
(l) performing a ECG; and
(k) performing a blood test.

Preferably, when it is determined the patient has, by a second evaluation any one or more of: sub-threshold racing thoughts, creativity, successful careers, academic performance, being able to perform tasks effectively before or together with depression, agitation, anxiety, and bipolarity, the method further comprises any one or more of discontinuation, reduction, gradual tapering, of patient anti-depressant drug treatment.

Conveniently, wherein upon any one or more of discontinuation, reduction, gradual tapering, of patient anti-depressant drug treatment is performed, the method further comprises instructing the patient to discontinue prior to treatment any one or more of: methylated xanthines in beverages and medications, alcohol, illicit drugs, stimulants including all energy drinks, sports drinks, decaffeinated beverages, and foodstuff marketed as energy boosting.

Preferably, the method further comprises instructing the patient to discontinue prior to treatment any one or more of: methylated xanthines in beverages and medications, alcohol, illicit drugs, stimulants including all energy drinks, sports drinks, any decaffeinated beverages, and foodstuff marketed as energy boosting.

Conveniently, the method further comprises instructing the patient to perform any one or more of, a ECG, a blood test. This provides for screening for use of medication.

Preferably, wherein upon evaluation determines the patient does have any one or more of:
sub-threshold racing thoughts, creativity, successful careers, academic performance, being able to perform tasks effectively with depression, agitation, anxiety, bipolarity the method further comprises administering any of:
(a) quetiapine including other mood destabilisers until the patient stabilises;
(b) right-sided 1 Hz rTMS or cTBS until the patient stabilises;
(c) right-sided 1 Hz rTMS or cTBS in combination with quetiapine until the patient stabilises; and
(d) right-sided rTMS or cTBS in combination with any one or more of a neuroleptic, a mood stabilise or in combination with levothyroxine from 50 mcgs to 1000 mcgs or liothyronine up to 160 mcgs.

Conveniently, wherein upon administering any one or more of:
(a) quetiapine, including other mood destabilisers until the patient stabilises;
(b) right-sided 1 Hz rTMS or cTBS until the patient stabilises;

(c) right-sided 1 Hz rTMS or cTBS in combination with quetiapine until the patient stabilises; and
(d) right-sided 1 Hz rTMS or cTBS in combination with any one or more of a neuroleptic, a mood stabiliser
(e) right sided 1 Hz rTMS or cTBS in combination with levothyroxine from 50 mcgs to 1000 mcgs or liothyronine up to 160 mcgs or Quetiapine.

and it is found, by evaluation that: sub-threshold racing thoughts, agitation, anxiety, bipolarity have suppressed, but patient depression still remains; the method further comprises initiating any one or more of, thyroxine, left-sided rTMS at 10 Hz, and a combination of the above.

Preferably, wherein upon evaluation determines the patient does not have any one or more of: sub-threshold racing thoughts, creativity, successful careers, academic performance, being able to perform tasks effectively with depression, agitation, anxiety, and bipolarity, but patient depression still remains; the method further comprises initiating thyroxine.

Conveniently, wherein upon evaluation determines the patient does not have any one or more of: sub-threshold racing thoughts, creativity, successful careers, academic performance, being able to perform tasks effectively with depression, agitation, anxiety, and bipolarity, but patient depression still remains; the method further comprises initiating left-sided rTMS at substantially 10 Hz.

Preferably, wherein upon evaluation determines the patient does not have any one or more of: sub-threshold racing thoughts, creativity, successful careers, academic performance, being able to perform tasks effectively with depression, agitation, anxiety, and bipolarity but patient depression still remains; the method further comprises initiating left-sided rTMS at substantially 10 Hz in combination with thyroxine.

Conveniently, the method further comprises in optional combination with the first and second evaluations, a third evaluation after rTMS treatment to determine if the patient has depression.

Preferably, the third evaluation comprises: performing an ECG; baseline thyroid function tests through a blood test and analysing the free-T4 and free-T3 ratio following the administration of thyroid hormone, levothyroxine sodium or levothyroxine, whereby the free-T4 rise is substantially higher than the free-T3 rise, with a rise in reverse T3. This provides for patient screening, indicating mixed states and/or bi-polarity.

Conveniently, when it is concluded that the patient does have depression, the patient is: further administered with any one or more of: left-sided rTMS treatment, prescribed with an increased dosage of thyroxine (or other thyroid hormone drug analogue, i.e. a compound having the same activity as thyroxine) of about 50 mcg to 1000 mcg.

Preferably, when it is concluded that the patient has experienced a significant reduction in depression, the method further comprises: administering a maintenance rTMS on a weekly basis thereafter for about 4-5 weeks, and then, administering a maintenance rTMS on a monthly basis thereafter.

According to a further aspect of the present invention, there is provided a method of performing a clinical procedure for use in the treatment of resistant depression, the method comprising: performing patient evaluation to determine symptoms of resistant depression, the patient evaluation comprising: a patient interview; a Hypomania Symptom checklist questionnaire completed by the patient; an observer interview; family history; and the method further comprising: instructing the patent to discontinue any one or more of methylated xanthines in beverages and medications, alcohol, illicit drugs, stimulants of all kinds, including all energy drinks, sports drinks, decaffeinated beverages, foodstuff marketed as energy boosting; and administering rTMS in combination with a medicament. This provides an improved treatment protocol whereby patients with a psychiatric condition such as bipolar disorder (either threshold or sub-threshold) and/or major depressive disorder, who could theoretically deteriorate on antidepressants (productive, creative, successful individuals), are treated in a specific way to ensure better results. Following this protocol compared with other techniques has shown substantially high success in treatment resistant cases.

According to a further aspect of the present invention, there is provided a method of performing a clinical procedure for use in the treatment of resistant depression, the method comprising: performing patient evaluation to determine symptoms of resistant depression, the patient evaluation comprising: a patient interview; a Hypomania Symptom checklist questionnaire completed by the patient; an observer interview; family history; the method further comprising: administering repetitive transcranial magnetic stimulation in alternate; the one of alternate comprising a first electromagnetic frequency and the other one of the alternate comprising a second electromagnetic frequency; wherein the one of the alternate comprises a first electromagnetic frequency less than the other one of alternate comprising a second electromagnetic frequency. This provides a further improved treatment protocol whereby patients with a psychiatric condition such as bipolar disorder (either threshold or sub-threshold) and/or major depressive disorder, who could theoretically deteriorate on antidepressants (productive, creative, successful individuals), are treated in a specific way to ensure better results. Following this protocol compared with other techniques has shown substantially high success in treatment resistant cases.

Apparatus

According to a further aspect of the present invention there is provided an apparatus for modulating a brain activity of a human patient, the apparatus comprising: evaluation means for determining symptoms of a psychiatric condition; and repetitive transcranial magnetic stimulation (rTMS) means for subjecting a patient to rTMS, the rTMS occurring at a concentrated region of the scalp, at preferred electromagnetic frequency, and for a time sufficient to modulate said brain activity wherein an improvement in psychiatric condition is achieved. This provides an improved modulation apparatus whereby patients with a psychiatric condition such as bipolar disorder (either threshold or sub-threshold) and/or major depressive disorder, who could theoretically deteriorate on antidepressants (productive, creative, successful individuals), are treated in a specific way to ensure better results.

Optionally, the rTMS means provides rTMS to the patient at about 10.1 Hz. Optionally, the rTMS means provides rTMS to the patient at about 0.9 Hz.

Preferably, the evaluation means provide: means for performing a patient interview; means for performing a Hypomania Symptom checklist (HCL-32) questionnaire; means for performing an observer interview; and means for analysing family history.

Further Methods of Medical Treatment

According to a further aspect of the present invention there is provided the use of a medicament as described herein in the preparation of a medicament composition for the treatment of a psychiatric condition. Suitably, before, after or simultaneously to the use of said medicament composition, rTMS is provided the patient. Suitably, rTMS may be provided as described herein. Suitably the medicament is for treating thyroid dysfunction, or for modulating the amount or activity or ratio or a combination thereof of a thyroid hormone(s) present in the subject, for example in embodiments a treatment may be a treatment for thyroid dysfunction.

According to a further aspect of the present invention there is provided a medicament for use in the treatment of a psychiatric condition. Suitably a psychiatric condition may be selected for example from bipolar disorder (either threshold or sub-threshold) and/or major depressive disorder or resistant depression. Suitably before, after or simultaneously to the use of said medicament, rTMS is provided the patient. Suitably, rTMS may be provided as described herein. Suitably the medicament is for treating thyroid dysfunction or for modulating the amount or activity or ratio or a combination thereof of a thyroid hormone(s) present in the subject. As will be appreciated in the art, thyroid hormones are typically considered to be two hormones produced and released by the thyroid gland, namely triiodothyronine (T3) and thyroxine (T4). Bipolar, RD and ADHD patients have an inability to convert T4 into T3 resulting in cerebral thyroid deficiency.

Suitably a medicament may exclude any one or more of methylated xanthines in beverages and medications, alcohol, illicit drugs, stimulants of all kinds, including all energy drinks, sports drinks, decaffeinated beverages, foodstuff marketed as energy boosting. Suitably the medicament is for treating thyroid dysfunction as described above.

According to a further aspect of the present invention there is provided a medicament for use in the treatment of a psychiatric condition, for example bipolar disorder (either threshold or sub-threshold) and/or major depressive disorder or resistant depression or ADHD, wherein the medicament is administered to a subject/patient as part of a treatment regimen wherein the subject has been provided with rTMS, before treatment with medicament, will be provided with rTMS after treatment with medicament, or is simultaneously treated with rTMS and provided with the medicament. Suitably the medicament is for treating thyroid dysfunction, Suitably the medicament is for treating thyroid dysfunction, or for modulating the amount or activity or ratio or a combination thereof of a thyroid hormone(s) present in the subject, for example in embodiments. Suitably a medicament may exclude any one or more of methylated xanthines in beverages and medications, alcohol, illicit drugs, stimulants of all kinds, including all energy drinks, sports drinks, decaffeinated beverages, foodstuff marketed as energy boosting.

Suitably, the medicament may be used in the treatment of psychiatric condition in a subject in an administration pattern wherein the medicament is provided pre, post or simultaneously with rTMS.

Assay

According to a further aspect of the present invention there is provided an assay, (for example a companion diagnostic assay which provides information to improve the effectiveness of rTMS or a medicament for use in the treatment of a psychiatric condition in combination with a rTMS treatment of a subject, for example wherein rTMS is provided before treatment with medicament, will be provided with rTMS after treatment with medicament, or is simultaneously treated with rTMS and provided with a medicament, and/or monitor response to treatment) wherein the assay comprises the step of determining thyroid function as described.

Suitably the assay may be an in vitro assay and the method comprises the step of identifying the presence or deficiency of one or more enzymes involved in thyroid hormone activation over a control level or genes coding for carrier proteins. Suitably a control level may be determined from a population not suffering from a psychiatric condition. Suitably, the method may identify the presence or deficiency of enzymes involved in thyroid hormone activation relative to a control level. Suitably, the method may identify the presence or deficiency of one or more enzymes involved in thyroid hormone activation in the brain. Suitably, the method may identify patients having difficulty in converting T4 (thyroxine) to T3 (active thyroid hormone). Suitably, the method may identify a Deiodinase enzyme deficiency. Suitably the method may identify a genetic polymorphism in a subject/patient which provides for a presence or deficiency of one or more enzymes involved in thyroid hormone activation over a control level, for example a polymorphism of a genetic sequence controlling the production, release, activity, or ratio of triiodothyronine (T3) and thyroxine (T4 or a deficiency in the function or production of the thyroid hormones carrier proteins).

Kit

According to a further aspect of the invention there is provided a kit comprising an assay capable of determining or identifying the presence or deficiency of one or more enzymes involved in thyroid hormone activation over a control level or genes coding for carrier proteins as discussed above, for example by detecting a genetic polymorphism and a device to provide rTMS and/or a medicament for use to treat a psychiatric condition.

Further Aspects of the Invention are Described Below:

1. A method of modulating a brain activity of a human patient, the method comprising: performing patient evaluation (106, 114, 202, 218) to determine symptoms of a psychiatric condition; and subjecting a patient to a repetitive transcranial magnetic stimulation (rTMS) (204, 214, 216), the rTMS occurring at a concentrated region of the scalp, at preferred electromagnetic frequency, and for a time sufficient to modulate said brain activity wherein an improvement in a psychiatric condition is achieved.

2. A method of modulating a brain activity of a human patient according to clause 1, wherein the rTMS further occurs at different concentrated regions of the scalp, normally between time periods of rTMS treatment.

3. A method of modulating a brain activity of a human patient according to clause 2, wherein the different concentrated regions of the scalp comprise a substantially left dorsolateral prefrontal cortex (DLPFC) region and a substantially right dorsolateral prefrontal cortex (DLPFC) region.

4. A method of modulating a brain activity of a human patient according to clause 1, wherein the preferred electromagnetic frequency is below about 20.1 Hz.

5. A method of modulating a brain activity of a human patient according to clause 1, wherein the preferred electromagnetic frequency is above about 0.9 Hz.

6. A method of modulating a brain activity of a patient according to clause 1, wherein the patient evaluation (218) comprises: administering a medicament selected from any one or more of: levothyroxine and thyroxine; Liothyronine performing an ECG; and analysing the free-T4 and free-T3 rise ratio following the initiation of thyroid hormone treatment and the rT3 rise; the arrangement being such that when the free-T4 rise is substantially higher than the lagging free-T3 rise and a rise of rT3, an indication of bipolarity is determined.

7. A method of modulating a brain activity of a human patient, the method comprising: performing patient evaluation (106, 114, 202) to determine symptoms of a psychiatric condition; and subjecting a patient to a repetitive transcranial magnetic stimulation (rTMS) (204, 214, 216) in combination with a medicament, the rTMS in combination with the medicament occurring for a time sufficient to modulate said brain activity wherein an improvement in a psychiatric condition is achieved.

8. A method of modulating a brain activity of a human patient according to clause 7, wherein a medicament is selected from a group consisting of neuroleptic and a mood stabiliser.

9. A method of modulating a brain activity of a human patient according to anyone of clauses 7 to 8, wherein a medicament comprises a combination of neuroleptics and mood stabilisers, excluding anti-depressants.

10. A method of modulating a brain activity of a human patient according to any one of clauses 7 to 9, wherein the medicament is selected from at least one medicament selected from quetiapine, thyroxine, levothyroxine, liothyronine and levothyroxine sodium.

11. A method of modulating a brain activity of a human patient according to any one of clauses 7 to 10, wherein the medicament comprises at least 50 mg of quetiapine.

12. A method of modulating a brain activity of a human patient according to any one of clauses 7 to 11, wherein the medicament comprises at least 50 mcg of thyroxine.and/or 10 mcg of Liothyronine 13. A method of modulating a brain activity of a human patient according to any one of clauses 7 to 12, wherein the medicament comprises at least 50 mcg of levothyroxine and/or 10 mcg of liothyronine.

14. A method of modulating a brain activity of a human patient according to any one of clauses 6 to 13, wherein the medicament comprises at least 50 mcg thyroxine and/or liothyronone of at least 10 mcg and at least 50 mg of quetiapine.

15. A method of modulating a brain activity of a human patient, the method comprising: performing patient evaluation (106, 114, 202) to determine symptoms of a psychiatric condition; and administering repetitive transcranial magnetic stimulation in alternate; the one of alternate comprising a first electromagnetic frequency (204) and the other one of the alternate comprising a second electromagnetic frequency (214); wherein the one of the alternate comprises a first electromagnetic frequency less than the other one of the alternate comprising a second electromagnetic frequency.

16. A method of modulating a brain activity of a human patient according to clause 15, wherein the one of the alternate electromagnetic frequency (204) is substantially 1 Hz and the other one of the alternate electromagnetic frequency (214) is substantially 10 Hz.

17. A method of modulating a brain activity of a patient according to clause 15, wherein the one of the alternate (204) is performed at a substantially right region DLPFC of the scalp at an electromagnetic frequency of substantially 1 Hz or cTBS and other one of the alternate (214) is performed at a substantially left DLFPC region of the scalp at an electromagnetic frequency of substantially 10 Hz. or iTBS 18. A method of modulating a brain activity of a patient according to clause 15, wherein rTMS (204, 214) is performed in combination with a medicament.

19. A method of performing a clinical procedure for use in the treatment of resistant depression, the method comprising: performing a first patient evaluation (106) to determine symptoms of resistant depression, the first patient evaluation comprising: a patient interview; a Hypomania Symptom checklist (HCL-32) questionnaire completed by the patient; an observer interview; and family history; the method further comprising: administering rTMS (204, 214, 216) to at least one concentrated scalp region of the patient, based on the result(s) of said evaluation.

20. A method according to clause 19 wherein the first patient evaluation (106) further comprises investigating for any one or more of:
(a) signs of sub-threshold racing thoughts;
(b) signs of bi-polarity;
(c) signs of mixed states;
(d) signs of insomnia;
(e) anxiety anti-depressants;
(f) sub-threshold signs of racing thoughts;
(g) creativity;
(h) successful careers;
(i) academic performance;
(j) being able to perform tasks effectively with depression;
(k) agitation;
(l) racy thoughts;
(m) signs of productivity; and
(n) if the patient can multi-task.

21. A method according to clause 19 wherein the first patient evaluation (106) is further used to determine if a patient has any one or more of: sub-threshold racing thoughts, creativity, successful careers, academic performance, being able to perform tasks effectively with depression, agitation, anxiety, and bipolarity.

22. A method according to clause 21 wherein upon determining the patient has any one or more of: sub-threshold racing thoughts, creativity, successful careers, academic performance, being able to perform tasks effectively with depression, agitation, anxiety, and bipolarity; the method further comprises any one or more of: discontinuation, reduction, and gradual tapering of patient anti-depressant drug treatment (108).

23. A method according to clause 21 wherein upon determining the patient does not have any one or more of: sub-threshold racing thoughts, creativity, successful careers, academic performance, being able to perform tasks effectively with depression, agitation, anxiety, and bipolarity; the method further comprises analysing the patient HCL-32 (110).

24. A method according to clause 23 wherein upon analysing the patient HCL-32 (110), and upon the result of the patient HCL-32 being greater than 14 (110), the method further comprises any one or more of: discontinuation, reduction, and gradual tapering of patient anti-depressant drug treatment (112).

25. A method according to clause 23 wherein upon referring to the patient HCL-32, and upon the result of the patient HCL-32 being lower than 14 (110) the method further comprises: performing a second evaluation (114); the second evaluation being used to determine if the patient has any one or more of: sub-threshold racing thoughts, creativity, successful careers, academic performance, being able to perform tasks effectively with depression, agitation, anxiety and bipolarity.

26. A method according to clause 25 wherein the second evaluation (114) comprises investigating for any one or more of:
(a) a patient prospective mood chart;
(b) generally being jovial without exhibiting signs of bipolarity;
(c) a history of becoming any one or more of anxious, agitated with exposure to antidepressants;

(d) a history of any signs of slight mood elevation whether any one or more of sustained, episodic;
(e) the level of the patient pre morbid functioning being higher than normal;
(f) a bipolar spectrum;
(g) premorbid ICD-10 subthreshold hypomania;
(h) mild signs of cyclothymia;
(i) sub-threshold bipolarity;
(j) performing a ECG; and
(k) performing a blood test.

27. A method according to clause 25 wherein when it is determined the patient has, by a second evaluation (114) any one or more of: sub-threshold racing thoughts, creativity, successful careers, academic performance, being able to perform tasks effectively with depression, agitation, anxiety, bipolarity; the method further comprises any one or more of discontinuation, reduction, and gradual tapering of patient anti-depressant drug treatment (116).

28. A method according to any one of claims 22, 24, or 27 wherein upon any one or more of discontinuation, reduction, gradual tapering, of patient anti-depressant drug treatment is performed, the method further comprises instructing the patient to discontinue, prior to treatment, any one or more of: methylated xanthines in beverages and medications, alcohol, illicit drugs, stimulants including all energy drinks, sports drinks, decaffeinated beverages (105), and foodstuff marketed as energy boasting.

29. A method according to clause 19 wherein the method further comprises instructing the patient to discontinue prior to treatment any one or more of: methylated xanthines in beverages and medications, alcohol, illicit drugs, stimulants including all energy drinks sports drinks, decaffeinated beverages (105), and foodstuff marketed as energy boasting.

30. A method according to clause 19 wherein the method further comprises instructing the patient to perform any one or more of, a ECG, and blood test.

31. A method according to any one of clauses 21 or 25, wherein upon evaluation determines the patient does have any one or more of: sub-threshold racing thoughts, creativity, successful careers, academic performance, being able to perform tasks effectively with depression, agitation, anxiety, bipolarity the method further comprises administering any one or more of (204): (a) quetiapine including other mood destabilisers until the patient stabilises; (b) right-sided 1 Hz rTMS until the patient stabilises; (c) right-sided 1 Hz rTMS or cTBS in combination with quetiapine until the patient stabilises; and (d) right-sided rTMS in combination with any one or more of a neuroleptic, a mood stabiliser. e) right-sided 1 Hz rTMS or cTBS in combination with levothyroxine, levothyroxine sodium or liothyronine f) right-sided 1 Hz rTMS or cTBS in combination with a mood stabiliser and/or a neuroleptic with levothyroxine, levothyroxine sodium or liothyronine 32. A method according to clause 31, wherein upon administering any one or more of:
(a) quetiapine, including other mood destabilisers until the patient stabilises; b) Levothyroxine, levothyroxine sodium, liothyronine until the patient stabilises
(b) right-sided 1 Hz rTMS or cTBS until the patient stabilises;
(c) right-sided 1 Hz rTMS or cTBS in combination with quetiapine until the patient stabilises;
d) right-sided 1 Hz rTMS or cTBS in combination with quetiapine, levothyroxine, levothyroxine sodium or liothyronine until the patient stabilises; and
e) right-sided 1 Hz rTMS or cTBS in combination with any one or more of a neuroleptic, a mood stabiliser and it is found, by evaluation that any one or more of: sub-threshold racing thoughts, agitation, anxiety, and bipolarity have suppressed (208), but patient depression still remains (210); the method further comprises initiating any one or more of, thyroxine, left sided rTMS at 10 Hz, or iTBS and a combination of the above.

33. A method according to any one of clauses 21 or 25, wherein upon evaluation (106, 114, 202) determines the patient does not have any one or more of: sub-threshold racing thoughts, creativity, successful careers, academic performance, being able to perform tasks effectively with depression, agitation, anxiety, and bipolarity, but patient depression still remains (210); the method further comprises initiating thyroxine (214).

34. A method according to any one of clauses 21 or 22, wherein upon evaluation (106, 114, 202) determines the patient does not have any one or more of: sub-threshold racing thoughts, creativity, successful careers, academic performance, being able to perform tasks effectively with depression, agitation, anxiety, and bipolarity, but patient depression still remains (210); the method further comprises initiating left-sided rTMS at substantially 10 Hz (214).

35. A method according to any one of clauses 21 or 22, wherein upon evaluation determines the patient does not have any one or more of: sub-threshold racing thoughts, creativity, successful careers, academic performance, being able to perform tasks effectively with depression, agitation, anxiety, and bipolarity but patient depression still remains (210); the method further comprises initiating left-sided rTMS at substantially 10 Hz in combination with thyroxine (216).

36. A method according to clause 19, wherein the method further comprises in optional combination with the first and second evaluations, a third evaluation after rTMS treatment (216, 218) to determine if the patient has depression.

37. A method according to clause 36 wherein the third evaluation (218) comprises: performing an ECG; and analysing the free-T4 and free-T3 ratio following the initiation of thyroid hormone treatment, whereby the free-T4 rise is substantially higher than the free-T3 rise as well as a rise in rT3

38. A method according to any one of clauses 36 or 37, when it is concluded that the patient does have depression, the patient is: further administered with any one or more of: left-sided rTMS treatment (216); an increased dosage of thyroxine of about 50 mcg to 1000 mcg (216).

39. A method according to any one of clauses 36 or 37, when it is concluded that the patient has experienced a significant reduction in depression, the method further comprises: administering a maintenance rTMS on a weekly basis thereafter for about 4-5 weeks, and then, administering a maintenance rTMS on a month basis thereafter (220).

40. A method of performing a clinical procedure for use in the treatment of resistant depression, the method comprising: performing patient evaluation (106) to determine symptoms of resistant depression, the patient evaluation comprising: a patient interview; a Hypomania Symptom checklist questionnaire (HCL 32) completed by the patient; an observer interview; family history; and the method further comprising: instructing the patent to discontinue any one or more of methylated xanthines in beverages or medications, alcohol, illicit drugs, stimulants of all kinds, including all energy drinks, sports drinks, decaffeinated beverages, foodstuff marketed as energy boasting (118); and administering rTMS in combination with a medicament (204, 216).

41. A method of performing a clinical procedure for use in the treatment of resistant depression, the method comprising: performing patient evaluation to determine symptoms of resistant depression, the patient evaluation comprising: a patient interview; a Hypomania Symptom checklist questionnaire completed by the patient;
an observer interview; family history; and the method further comprising: administering repetitive transcranial magnetic stimulation in alternate; the one of alternate comprising a first electromagnetic frequency (204) and the other one of the alternate comprising a second electromagnetic frequency (214); wherein the one of the alternate comprises a first electromagnetic frequency less than the other one of alternate comprising a second electromagnetic frequency.

42. An apparatus for modulating a brain activity of a human patient, the apparatus comprising: evaluation means (106) for determining symptoms of a psychiatric condition; and
repetitive transcranial magnetic stimulation (rTMS) means (204) for subjecting
a patient to rTMS, the rTMS occurring at a concentrated region of the scalp, at preferred electromagnetic frequency, and for a time sufficient to modulate said brain activity wherein an improvement in a psychiatric condition is achieved.

43. An apparatus for modulating a brain activity of a human patient according to clause 42, wherein the rTMS means provides rTMS to the patient at about 10.1 Hz.

44. An apparatus for modulating a brain activity of a human patient according to any one of clauses 42 or 43, wherein rTMS means provides rTMS to the patient at about 0.9 Hz.

45. An apparatus for modulating a brain activity of a human patient according to any one of clauses 42 to 44, wherein the evaluation means (104) provide: means for performing a patient interview; means for performing a Hypomania Symptom checklist (HCL-32) questionnaire; and means for analysing family history.

Preferred features and embodiments of each aspect of the invention are as for each of the other aspects mutatis mutandis unless context demands otherwise.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness.

Reference to cited material or information contained in the text should not be understood as a concession that the material or information was part of the common general knowledge or was known in any country.

As used herein, the articles "a" and "an" refer to one or to more than one (for example to at least one) of the grammatical object of the article.

"About" shall generally mean an acceptable degree of error for the quantity measured given the nature or precision of the measurements.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

FIGURES

Figure 2:
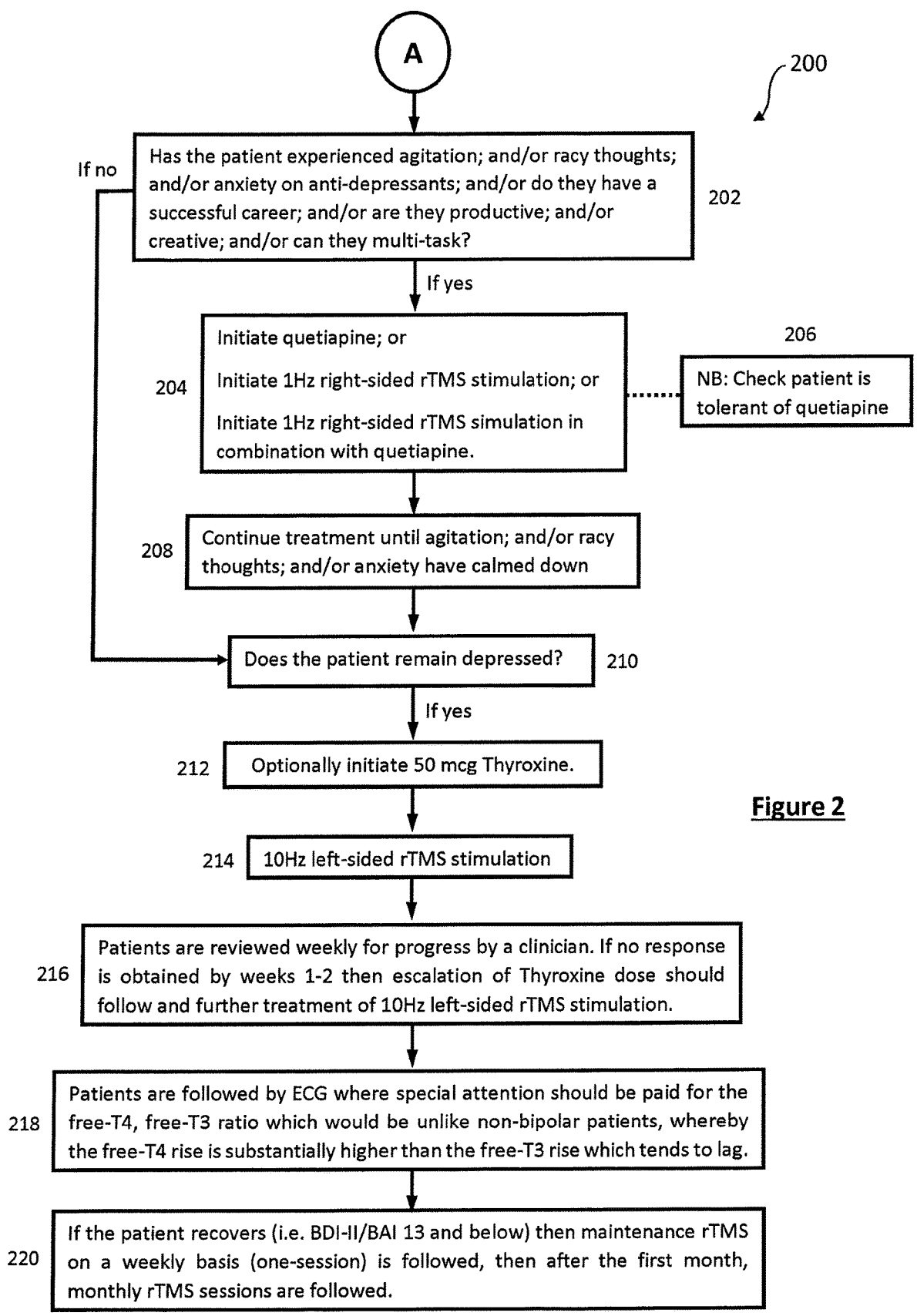

The above and other aspects of the present invention will now be described in further detail by way of example only, and with reference to the accompanying drawings, in which:

FIG. 1 is a flow chart illustrating exemplary embodiments of methods of the present invention that may be used for patient evaluation; and FIG. 2 is a flow chart illustrating exemplary embodiments of methods of the present invention that may be used for an rTMS treatment protocol.

Referring to FIG. 1, a patient evaluation and analysis process 100 is provided. This relates to a psychiatric history examination. Preferably, the patient evaluation is performed to determine symptoms of a physiological and/or psychiatric condition, and even more preferably, to determine symptoms of resistant depression. The results from patient evaluation are typically analysed by a healthcare professional.

At step 102, evaluation, the patient performs a routine psychometric test. For example, a Beck Depression Inventory (BDl-II) and Beck Anxiety Inventory (BAI). At step 104, evaluation, the patient is then asked to complete a Hypomania Symptom Checklist (HCL-32) questionnaire. The tests and questionnaires provide background history about the patient. In some cases these tests and questionnaires may be performed in the clinic, or in further cases, the patient may have been expected to complete the tests and questionnaires before an appointment with a healthcare professional (i.e. offsite).

During first evaluation and analysis, 106, the patient is interviewed, to determine symptoms of resistant depression. The first patient evaluation 106 is further used to determine if a patient has: sub-threshold racing thoughts; and/or creativity; and/or successful careers; and/or academic performance; and/or being able to perform tasks effectively before or together with depression; and/or agitation; and/or anxiety; and/or bipolarity.

The evaluation process further comprises asking if he or she has experienced any one or more of the following:—
racing thoughts, bi-polarity; and/or insomnia; mixed states;
anxiety on previous or current anti-depressants; and/or
any sub-threshold signs of racing thoughts; and/or
any current and/or previous signs of creativity; and/or
any current and/or previous successful careers; and/or
any current and/or previous academic performance; and/or
being able to perform tasks effectively before or together with depression; and/or
agitation; and/or
racy thoughts; and/or
signs of productivity; and/or
can the patient multi-task?

A relative and/or an observer interview may be performed with referencing towards family history. If during any one or more of this evaluation a positive outcome is from any one or more of the above, then at step 108, antidepressant treatment is discontinued and/or reduced and/or tapered gradually. The process then continues at step 118, proceeding thereon.

If the answer is no, then reference to HCL-32 at step 110 is made. At step 110, evaluation, with reference to the completed questionnaire at 104, the patient HCL-32 results are analysed to see if the store is greater than 14. If the results are greater than 14, then at step 112, anti-depressant treatment is discontinued, reduced or tapered gradually. The process then continues at step 118, proceeding thereon.

If the HCL-32 is less than 14, then at step 114 the patient is analysed, evaluated and interviewed further, at a second evaluation. Again, particular attention is paid to receiving a positive outcome in response to questions and/or analysis and/or evaluation. A positive outcome being received from sub-threshold racing thoughts; and/or creativity; and/or successful careers and/or academic performance; and/or being able to perform tasks effectively before or together with depression; and/or agitation; and/or anxiety; and/or 10 bipolarity.

In addition to the first evaluation steps asked at step 106, the second evaluation may also comprise any one or more of the following:—
- a reference towards a patient prospective mood chart; and/or
- a relative/observer interview; and/or
- evaluation of patient family history; and/or
- generally being jovial without exhibiting signs of bipolarity; and/or
- investigating for a history of becoming anxious or agitated with exposure to antidepressants; and/or
- a history of any signs of slight mood elevation whether sustained or episodic; and/or
- investigating the level of the patient premorbid functioning being higher than normal; and/or
- performing a blood test to exclude organic mood disorder; and/or
- performing and analysing a baseline ECG; and/or
- investigating a bipolar spectrum; and/or
- investigating for the emergence of mixed states, including any one or more of: racing thoughts, and/or depression, and/or insomnia, and/or agitation; and/or
- investigating for premorbid ICD-10 subthershold hypomania; and/or
- investigating for mild signs of cyclothymia; and/or
- investigating for sub-threshold bipolarity
- an ECG
- a blood test Furthermore, a high degree of suspicion may be actioned towards the patient's condition. Patient evaluation may also comprise investigating the level of the patient premorbid functioning. Further patient evaluation may also comprise further interviewing of family, friends, close relatives or the like and/or with or without a high degree of suspicion. It should be noted any one or more of the following above evaluation steps may also occur at step 106.

If a positive outcome is received, then at step 116 anti-depressant treatment is discontinued, reduced or tapered gradually. The process then continues at step 118, proceeding thereon.

Prior to treatment, at step 118 the patient is instructed to discontinue any one or more of:—
- methylated xanthines in beverages or medications; and/or
- alcohol including alcoholic beverages; and/or
- illicit drugs; and/or
- stimulants of all kinds, including all energy drinks and/or sports drinks; and/or
- any decaffeinated beverages; and/or
- foodstuff marketed as energy boasting It is understood that the definition of "illicit" may vary in definition by country to country. Illicit can mean "illegal", "non-prescribed", or "non-medically prescribed". "Food stuff marketed as energy boasting" may include for example, boast bars, energy bars and/or tablets, and/or supplements that are taken in addition to a main meal.

Prior to treatment, patients undergo blood tests at step 120 to exclude organic mood disorder. Results are reviewed accordingly at step 122. Patients undergo a baseline ECG at step 210. Based on the results of the blood test and/or a baseline ECG, anti-depressant treatment may also be discontinued, reduced or tapered gradually. The method then proceeds from thereon.

Initial patient evaluation ends at step 124 after baseline ECG, and continues via connector A towards the treatment protocol in FIG. 2.

Referring to FIG. 2, at step 202, in accordance with prior first 106 and second 114 evaluation, the patient is evaluated to determine if they have experienced any one or more of the following:
- agitation; and/or
- racy thoughts; and/or
- anxiety on anti-depressants; and/or
- do they have a successfully career; and/or
- academic performance;
- being able to perform tasks effectively before or together with depression;
- bipolarity;
- are they productive; and/or
- are they creative; and/or
- can they multi-task If a positive outcome is received, i.e. the answer is yes to any one or more of the above it is important that the agitation; and/or racy thoughts; and/or anxiety are suppressed. If the answer is no, i.e. a negative response is obtained, then step 210 begins.

In some cases, at step 204, quetiapine can be started and pitched at a minimum of 50 mg. Before administering quetiapine, at step 206, it is important to determine if the patient is intolerant or cannot accept. If this is the case, then quetiapine is withheld, and other neuroleptics and/or mood stabilisers may be considered instead of quetiapine.

Additionally, 50 mcg of thyroxine may be administered. 50 mcg of levothyroxine or levothyroxine sodium may also be administered. A combination may also be administered, for example at least 50 mcg thyroxine and at least 50 mg of quetiapine. Throughout the treatment process an increased dosage of thyroxine of about 50 mcg to 1000 mcg may occur. Other quantities quetiapine, levothyroxine or levothyroxine sodium may include 50 mcg to 400 mcg, 50-650 mcg, 100 mcg to 500 mcg, 250 mcg to 600 mcg, 100 mcg to 650 mcg, 50 mcg to 200 mcg, 400 mcg to 1000 mcg.

For example, when used in combination, from 25-800 mgs of quetiapine or according to blood levels to 50 mcg-1000 mcg of levothyroxine, or liothyronine 10 mcg-160 mcg.

1 Hz (electromagnetic frequency) right-sided stimulation (inhibitory treatment) is used until the patient stabilises, wherein the preferred electromagnetic frequency is above about 0.9 Hz and wherein the preferred electromagnetic frequency is below about 20.1 Hz.

In some further cases, 1 Hz right-sided stimulation in combination with quetiapine may also be administered.

At step 208, the treatment is continued until agitation; and/or racy thoughts; and/or anxiety have calmed.

At step 210 the patient is asked if they still remain depressed.

If the answer is yes, then in some optional cases, at step 212, thyroxine treatment is initiated, which is initiated at 50 mcg, and kept at this level for a period of a week during the initial phases of rTMS treatment. In further cases, rTMS is administered without administering thyroxine at step 214.

At step 214, left-sided rTMS is performed, at an electromagnetic frequency of preferably about 10.1 Hz (electromagnetic frequency). Preferably, the electromagnetic frequency is below about 20.1 Hz. Preferably, the electromagnetic frequency is above about 0.9 Hz.

At step 216, patients are followed weekly for progress by a clinician. Special attention is paid to any emergence of mixed states, for example; agitation; and/or racy thoughts;

and/or anxiety. If the later are present, then 1 Hz right-sided stimulation is used until the patient stabilises. This runs alongside quetiapine.

Further treatment of 10 Hz left-sided stimulation should be administered if the patient is intolerant, depression remains, or is not accepting of the treatment, or no response is obtained by 4-5 weeks. Escalation of thyroxine should follow by 50 mcg every three to seven days. An increased dosage of thyroxine of about 50 mcg to a range of up to 1000 mcg may occur. Other quantities may include 50 mcg to 400 mcg, 100 mcg to 500 mcg, 250 mcg to 600 mcg, 100 15 mcg to 650 mcg, 50 mcg to 200 mcg, 400 mcg to 600 mcg.

ECG and blood tests of full thyroid functioning including TSH, Free T4 and Free T3 are followed.

At step 218, a third evaluation in combination with previous evaluations is performed to determine if the patient still has depression. This can be performed before or after rTMS treatment.

Using ECG, special attention should be paid for the free-T4, free-T3 rise ratio following initiation of thyroid which would be unlike non-bipolar patients, whereby the free T4 rise is substantially higher than the free-T3 rise which tends to lag. The improved method generally comprises administering levothyroxine and/or thyroxine. Then, performing a patient ECG and analysing the free-T4 and free-T3 ratio whereby the free-T4 rise is substantially higher than the lagging free-T3 rise after high dose Levothyroxine and/or thyroxine is used. rT3 also rises significantly This is unlike non-bipolar patients. If it is deemed helpful, in some cases, a patient ECG is also performed prior to administering levothyroxine and/or thyroxine.

If the patient experiences no mixed states, indicating a significant reduction in depression, then at step 220, following remission of depression, maintenance rTMS on a weekly basis (one-session) is followed for the first month (4-5 weeks), then after the first month, monthly rTMS sessions are followed.

Optionally, after receiving the rTMS treatment, analysis is made to determine if the patient has recovered using BDII and BAI II, having a cut-off point of 13 and below. Similarly, if the patient has recovered, then maintenance rTMS on a weekly basis (one-session) is followed for the first month, where monthly rTMS sessions are followed. If this is not possible, then cumulative number of sessions is administered over 2-3 months.

If the patient has not recovered with only depression rather than mixed symptoms or cycling, then, left sided 10 Hz stimulation is followed. Following this, patients are reviewed weekly for progress by a clinician.

Generally, rTMS treatment is performed at the patients scalp at preferred electromagnetic frequency, and for a time sufficient to modulate said brain activity wherein an improvement in a physiological condition is achieved. The anxiety and/or mixed states treatment is performed at a substantially right region dorsolateral prefrontal cortex (DLPFC) of the scalp at substantially 1 Hz and the depression rTMS treatment is performed at a substantially left DLFPC region of the scalp at substantially 10 Hz.

Example 1—in High Dose Levothyroxine (HDL) Combined with rTMS in 2 Patients

Case Report 1

A 23-year-old woman with a family history of rapid cycling bipolar Disorder presented with fatigue, over-eating, over-sleeping, low mood & passive suicidal ideation, alternating with mixed affective episodes, namely, depression with flight of ideas complicated by agitation, irritability and anger.

She also exhibited phases of hypomania (increased energy associated with marked feelings of well-being and happiness).

She was taking high dose Citalopram which is contraindicated.

Beck Depression Inventory Score was 38 in keeping with severe depression, Beck anxiety inventory 20 and HCL-32 questionnaire was 29 in keeping with an 80% probability of bipolar depression.

A diagnosis of rapid cycling bipolar disorder (RCBPD) was made.

Comprehensive blood tests excluded an organic cause. She started taking Levothyroxine 50 mcg od and increased gradually to supraphysiological doses.

Quetiapine, at a licensed dose, was prescribed but discontinued because of weight gain. rTMS was commenced, and she reported significant improvements in her mood but remained symptomatic.

One month later, she had racing thoughts and increased energy levels. The dose of Levothyroxine increased to 400 mcg once daily.

Two months later she was in remission and reported feeling the best in a long time. HDL was increased to 500 mcg o. d. for minor residual depressive symptoms. She remains in remission over a year later on HDL including maintenance rTMS with no side effects.

Taking Levothyroxine 500 mcg o. d., ECG: sinus rhythm, normal QTc. She was clinically euthyroid. Blood tests: TSH<0.01 miu/L (0.27-4.2), fT4 37.1 pmol/L (12-22), f3 8.4 pmol/L (3.1-6.8). Reverse T3: 30 ng/dL (10-24). Genetic analysis: wild type DIO1, heterozygote polymorphism of DIO2 gene (rs225014; T92A).

Case Report 2

A 53-year-old woman presented with a mixed affective state Characterised by profound depression and flight of ideas such as relentless racing thoughts, agitation, distress, hopelessness and intense suicidal thoughts.

She was diagnosed with ADHD and bipolar disorder with the latter being poorly treated. Her mood deteriorated substantially following a trip to Australia.

Quetiapine was started, and the dose escalated to 700 mg daily which partially helped her mood. Levothyroxine 50 mcg once daily was commenced and the dose slowly escalated to 400 mcg once daily and her mood stabilised. ECG showed sinus rhythm, rate 63 bpm.

She unfortunately suffered a relapse a few months later taking these 2 medications and so rTMS was commenced.

HDL was eventually increased 750 mcg once daily. This, together with rTMS achieved remission, with no side effects.

She has been in complete remission with HDL 750 mcgs OD, Quetiapine 700 mgs OD and maintenance rTMS for over a year. She reported no side effects and no symptoms of thyrotoxicosis.

On examination, pulse was 85 bpm and regular, weight 71 kg (no unintentional weight loss). She is clinically euthyroid.

TSH is suppressed, fT4 77.3 pmol/L (12-22), fT3 11.7 pmol/L (3.1-6.8) and reverse T3 elevated: 79 ng/dl (10-24). Pre-Levo-thyroxine thyroid function was normal: TSH 2.20 miu/L (0.27-4.2), fT4 12.3 pmol/L and fT3 3.6 pmol/L (same reference ranges or fT4 and fT3). She had a heterozygote polymorphism of both the DIO2 (rs225014; T92A) and DIO1 gene (rs2235544; 34C>A).

DISCUSSION

Two cases of patients with RCBPD, resistant to standard treatments are described who achieved remission of disease using high dose levothyroxine with rTMS.

There is an association between BPD and dysfunction of the thyroid (HPT) axis.

Thyroid disease is more likely to be presently in more resistant and rapid cycling forms of BPD. Contentiously, frank disturbances in the HPT axis are unusual in rapid cycling bipolar disorder. Instead a "latent hypofunction of the thyroid axis" has been suggested as a possible mechanism for the response to high dose Levothyroxine.

Studies have shown that high dose Levothyroxine helped achieve remission in rapid cycling bipolar disorder and was safe with no features of thyrotoxicosis.

Both our patients had a heterozygote polymorphism of the DIO2 gene and interestingly, an elevated fT4:fT3 ratio.

CONCLUSION

Rapid cycling bipolar disorder and mixed state affective states are dangerous conditions with high mortality and morbidity rates.

Standard treatments are often ineffective.

Data highlights an association between polymorphisms of the DIO2 gene and bipolar disorder We speculate that BPD is a form of cerebral hypothyroidism and that HDL helps to overcome the deficit while robust inactivating deiodinases in the periphery protect from systemic thyrotoxicosis.

This is evidenced by findings of normal clinical examination and elevated rT3.

rTMS exercises its well established neuroplastic effect, helping to achieve and maintain remission as an adjunct to HDL.

Example 2—in 20 Patients

Dr Andy Zamar (Consultant Psychiatrist), Dr Abbi Lulsegged (Consultant Endocrinologist), Dr Robin Roberts (Consultant Cardiologist) and their team at The London Psychiatry Centre have found through genetic testing that over 90% of the bipolar cases randomly and consecutively tested have a deficiency of one, two or both enzymes needed to activate thyroid hormone in the brain and the body.

These patients are unable to activate normal doses of thyroid hormone. The team found that as a result, they can be treated with minimal or no side effects with high dose thyroxine and rTMS, and some may need one additional drug as opposed to the usual requirement of a standard of 3 to 4 drugs which, as a rule, cause significant side effects.

Patients who had the combination of rTMS and high dose thyroid combination saw their condition recover fully after years of unsuccessful treatment with drugs (see below for details of the clinical trial). This effective new process also displays generally a lack of or minimal side effects, which is wonderful news for patients receiving the treatment.

The fact these patients did not suffer side effects on High dose Thyroxine has been previously reported but the reasons were never understood, and the treatment was never targeted to a specific identifiable population as this was never linked to any thyroid dysfunction, e.g. Deiodinase enzyme deficiency.

Clinical Trial

Retrospective analysis of 20 consecutive patients with RCBPD who achieved remission for a minimum of 6 months was undertaken.

All patients fulfilled the ICD-10 criteria for bipolar disorder and were strongly symptomatic. 17 were female, average age 32.4 yrs. All, except one had SNP of either DIO1, DIO2 or both. All but 2 patients were treated with rTMS to induce cerebral neuroplasticity.

Average pre-treatment fT4 was 17.0 pmol/L (12-22), and fT3 4.5 pmol/L (3.1-6.8), post treatment, FT4 was 59.7 pmol/L. and fT3 5.3 pmol/L. Average fT4:fT3 ratio pretreatment was 3.97:1, and post-treatment, was 5.26:1.

HDT range was 200-800 mcg for remission. Average of 472 mcg daily.

Discontinuation rate was 0%. One patient required dose reduction (750 mcg to 600 mcg) because of side effects. 12 patients needed 1 mood stabiliser.

HDL helps to overcome relative deficiency (cerebral) and that the polymorphisms of DIO1 and DIO2 play a role in this deficiency. (ii) Robust inactivating deiodinases in the periphery help protect from systemic thyrotoxicosis.

RCBPD is predominantly cerebral hypothyroidism, presenting with severe psychiatric symptomatology. HDT combined with rTMS for neuroplasticity is considered to be advantageous for remission of psychiatric symptoms.

Conventional protocols against treatment resistant patients are typically successful in about 25-30% of cases. The inventor has seen success rates of over 60% in real life drug resistant cases.

Recurrent depressive disorder patients will respond to left sided 10 Hz stimulation as per the normal protocol. Special care and attention has to be given to the sub-threshold bipolar population and/or major depressive disorder patients who could theoretically deteriorate or have deteriorated on antidepressants.

Although the invention has been particularly shown and described with reference to particular examples, it will be understood by those skilled in the art that various changes in the form and details may be made therein without departing from the scope of the present invention.

The invention claimed is:

1. A method of diagnosing and selecting patients with bipolarity or resistant depression for thyroxine treatment, wherein the method comprises:
    testing a patient for thyroid function, wherein the test for checking thyroid functions includes testing for the levels of free thyroxine (T4) and free triiodothyronine (T3) and wherein the test involves analysing the Free T4 and Free T3 ratio after administration of thyroxine, levothyroxine or an analogue or salt thereof whereby the Free T4 rise is higher than the lagging Free T3 rise; and
    diagnosing the patient as being bipolar or having resistant depression where it is determined by the testing that thyroid function exhibits a deficiency in at least one of thyroid hormone production, hormone activation, hormone use, and a deficiency in one or more intracellular carriers.

2. The method according to claim 1, wherein the deficiency is the inability to maintain normal physiological levels of T3 in the brain.

3. The method according to claim 1, wherein testing a patient for thyroid function comprises an electrocardiogram (ECG), or a blood test that is performed to test the levels of any one or more of the following: thyroid stimulating hormone (TSH), Free T4, Free T3 and reverse T3 (rT3).

4. The method according to claim 1, wherein the method comprises:
   a) performing an ECG on a patient, wherein the patient is a patient who has been administered with a medicament for treating thyroid dysfunction;
   b) analysing the free T4 and free T3 ratio after administration of the medicament; and
   c) selecting the patient for further treatment wherein there is a higher rise in the concentration of free T4 compared to the rise in concentration of free T3.

5. The method according to claim 1, wherein the method comprises:
   testing to detect polymorphisms in one or more enzymes involved in thyroid hormone function, and
   selecting the patient for treatment for being bipolar or having resistant depression where it is determined by the testing that there is an impairment in thyroid function.

6. The method of claim 5, wherein the method identifies polymorphisms which result in the patient having difficulty in converting T4 (thyroxine) to T3 (active thyroid hormone).

7. The method of claim 5, comprising detecting polymorphisms in any one of the following genes:
   a) DIO1 (Thyroxine Deiodinase Type I); DIO2 (Thyroxine Deiodinase Type II) or DIO3 (Thyroxine Deiodinase Type III), optionally wherein the polymorphism results in a reduction in the activity of the DIO1 and/or DIO2 and/or DIO3 proteins; or
   b) Intracellular carriers of T4/T3.

8. The method of claim 7, wherein the polymorphism is a single-nucleotide polymorphism (SNP),
   optionally wherein the SNP is any one or more of the following:
   a) rs2235544 (34C>A) in DIO1;
   b) rs12885300 (Gly3Asp) in DIO2; and/or
   c) Rs225014 (Thr92A1a).

9. A method of treating a patient presenting with resistant depression, ADHD or bipolarity, the method comprising:
   determining whether the patient has a dysfunctional thyroid, wherein an ECG or blood test is performed to test for thyroid functioning including:
      testing the levels of any one or more of the following: TSH, Free T4, Free T3, and rT3, and
      analyzing the Free T4 and Free T3 ratio whereby the rise in Free T4 is higher than the rise in Free T3, and if such is determined,
   administering to the patient a medicament for treating thyroid dysfunction, and subjecting the patient to repetitive transcranial magnetic stimulation (rTMS).

10. The method of claim 9, wherein the medicament increases the availability of cerebral T3.

11. The method of claim 9, wherein the medicament is selected from at least one of thyroxine, levothyroxine, liothyronine and levothyroxine sodium, optionally
   wherein the medicament also comprises a mood stabiliser or neuroleptic; or quetiapine.

12. The method of claim 11, wherein the medicament is one of the following combinations of medicaments:
   a) thyroxine and liothyronine; or
   b) thyroxine and quetiapine; or
   c) liothyronine and quetiapine; or
   d) thyroxine and liothyronine and quetiapine.

13. The method of claim 11, wherein the medicament comprises:
   a) at least 50 mcg of quetiapine;
   b) at least 50 mcg of thyroxine;
   c) at least 50 mcg of levothyroxine;
   d) at least 50 mcg thyroxine and at least 50 mcg of quetiapine; or
   e) at least 10 mcg of liothyronine.

14. The method of claim 9, wherein the medicament does not contain any antidepressants.

15. The method of claim 9, wherein the rTMS is performed at the following concentrated regions of the scalp:
   a) substantially left dorsolateral prefrontal cortex (DLPFC) region, preferably if flatly depressed; or
   b) substantially right dorsolateral prefrontal cortex (DLPFC) region, preferably if agitated, depressed, mixed, racy thoughts or rapid cycling.

16. The method of claim 9, wherein the preferred electromagnetic frequency for rTMS is: a) below about 20.1 Hz; or b) above about 0.9 Hz.

17. The method of claim 9, wherein:
   a) the left side of the brain is targeted with rTMS or intermittent theta burst rTMS (iTBS) when the patient is depressed; or
   b) the right side of the brain is targeted with rTMS or continuous theta burst rTMS (cTBS) when the patient is diagnosed as having a mixed condition.

18. The method of claim 9, wherein the rTMS is administered in alternate frequencies, said alternate frequencies being a first electromagnetic frequency and
   a second electromagnetic frequency, wherein the first electromagnetic frequency is about 1 Hz and the second electromagnetic frequency is about 10 Hz.

19. The method of claim 9, wherein the medicament also comprises a mood stabiliser or neuroleptic; and
   (a) wherein the medicament is least one selected from the group consisting of thyroxine, levothyroxine, liothyronine, and levothyroxine sodium; or
   (b) wherein the medicament is quetiapine.

20. The method of claim 9, further comprising testing a patient for thyroid function, wherein the test for checking thyroid function includes testing for the levels of free thyroxine and free triiodothyronine, and wherein the test involves analysing the Free T4 and Free T3 ratio after administration of thyroxine, levothyroxine, or an analogue or salt thereof whereby the Free T4 rise is higher than the lagging Free T3 rise.

* * * * *